United States Patent [19]

Hai et al.

[11] Patent Number: 5,041,615

[45] Date of Patent: Aug. 20, 1991

[54] PREPARATION OF BIS(SALICYL) DIESTERS

[75] Inventors: Ton T. Hai, Lake Villa; Deanna J. Nelson, Libertyville; Ana Srnak, Skokie, all of Ill.

[73] Assignee: Baxter International Inc., Deerfield, Ill.

[21] Appl. No.: 446,244

[22] Filed: Dec. 5, 1989

[51] Int. Cl.$^5$ .................... C07C 67/14; C07D 213/55
[52] U.S. Cl. ..................................... 560/143; 546/342
[58] Field of Search ........................ 560/143; 546/342

[56] References Cited

U.S. PATENT DOCUMENTS 874,929  12/1907  Berendes et al. ................... 560/143

OTHER PUBLICATIONS

Zaugg et al., *J. Biol. Chem.*, 225:2816, (1980).
Walder et al., *Biochem.*, 18:4265, (1979).

*Primary Examiner*—Jose G. Dees
*Assistant Examiner*—Vera C. Clarke
*Attorney, Agent, or Firm*—Sarah E. Bates; Paul C. Flattery; Robert E. Hartenberger

[57] ABSTRACT

Bis(salicyl) diesters useful as cross-linking agents for hemoglobin are prepared in high yield and purity by reacting salicylic acid or a derivative thereof with a lower aliphatic dicarboxylic acid halide in a lower aliphatic ketone or nitrile solvent in the presence of a pyridine derivative. The desired diester is recovered from the resulting insoluble pyridine derivative salt.

8 Claims, No Drawings

PREPARATION OF BIS(SALICYL) DIESTERS

FIELD OF THE INVENTION

The present invention relates to the preparation of bis(salicyl) diesters which are useful as agents for cross-linking subunits of hemoglobin.

BACKGROUND OF THE INVENTION

There is extensive interest in the development of blood substitutes and blood plasma expanders which can be easily prepared and used in place of donated blood. To be effective, such a substitute should be characterized by a sufficiently high oxygen-binding capacity for use under normal environmental conditions. It also should not be subject to renal elimination.

One type of substitute that has generated significant interest is modified hemoglobins A natural mammalian hemoglobin is a tetramer, i.e. it is characterized by four polypeptide chains, two identical alpha chains and two identical beta chains, that are noncovalently linked together. In plasma, oxygenated hemoglobin has a tendency to split into dimers, each of which is small enough to be filtered by the kidneys and excreted Such dimers thus potentially cause renal damage and have significantly decreased intravascular retention time.

A modified hemoglobin that has been described in the art is alpha, alpha-cross-linked hemoglobin. Such modified hemoglobin is described in U.S. Pat. Nos. 4,598,064 and 4,600,531 issued to Walder. The two alpha chains of the tetrameric hemoglobin molecule are cross-linked, specifically at Lys 99 Alpha 1 and Lys 99 Alpha 2. The cross-linking is effected by reaction of the hemoglobin with a bis(salicyl) diester, sometimes referred to as a "diaspirin" Walder's preferred cross-linking agent is bis(3,5-dibromosalicyl) fumarate.

The preparation of aspirin-based acylating and cross-linking agents for hemoglobin is described by Zaugg et al. in "Modification of Hemoglobin with Analogs of Aspirin," *J. Biol. Chem.*, 255:2816 (1980) and by Walder et al. in "Diaspirins that Cross-link Beta Chains of Hemoglobin: bis(3,5-dibromosalicyl) Succinate and bis(3,5-dibromosalicyl) Fumarate, *Biochem.*, 18:4265 (1979). The procedures described in these references suffer from certain disadvantages, particularly when used for large scale syntheses. For example, both the reaction medium (benzene) and the base (N,N-dimethylaniline) recommended by Walder are recognized carcinogens. In addition, isolation of the product by precipitation with dilute aqueous hydrochloric acid gives only moderate yields (on the order of 60 to 65 percent) of a crude product which contains an unacceptably high proportion of impurities. Unfortunately, these impurities also are difficult to remove. Repeated recrystallizations give low yields (25 to 30 percent) of pure bis(3,5-dibromosalicyl) fumarate. Accordingly, improvements on the process of Walder et al. are sought.

It is an object of the present invention to provide a process for the preparation of bis(salicyl) diester cross-linking agents in which the yields of desired product are enhanced in comparison to the yields obtainable using the prior art. It is a further object of this invention to develop such a process in which the use of benzene and N,N-dimethylaniline is eliminated.

SUMMARY OF THE INVENTION

The present invention, is an improved process for the preparation of a bis(salicyl) diester of the formula:

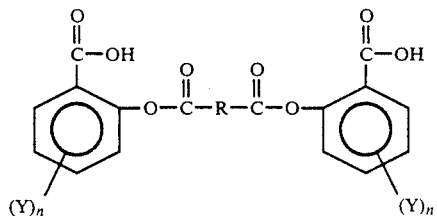

which involves the steps of:

(a) reacting an aromatic hydroxy acid of the formula:

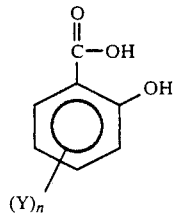

with a lower aliphatic dicarboxylic acid halide of the formula:

in a lower aliphatic ketone or nitrile solvent which contains an acid-accepting amount of a pyridine such as 2,6-lutidine to produce an insoluble bis(salicyl) diester-pyridine derivative salt;

(b) separating the insoluble bis(salicyl) diester pyridine derivative salt from the reaction mixture of step (a); and (c) recovering the desired bis(salicyl) diester from the insoluble bis(salicyl) diester-pyridine derivative salt; wherein R is a lower alkyl or alkylene of from 1 to about 5 carbon atoms; Y is hydrogen, chloro, bromo, iodo, fluoro, nitro, trifluoromethyl, or cyano; n is 1 or 2 and X is bromide or, preferably, chloride.

DETAILED DESCRIPTION OF THE INVENTION

The present invention provides an improved process for the preparation of bis(salicyl) diester cross-linking agents. Preferred bis(salicyl) diesters produced by the process of this invention are bis(3,5-dibromosalicyl) fumarate and bis(dibromosalicyl) succinate.

The process is initiated by reacting salicylic acid or a derivative thereof (hereinafter referred to as a "salicylic acid compound") of the formula:

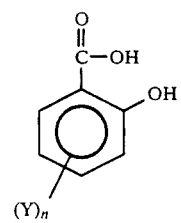

with a lower aliphatic dicarboxylic acid halide of the formula:

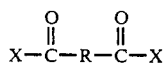

under ester-forming conditions to form a bis(salicyl) diester. Preferred lower aliphatic dicarboxylic acid halides are fumaroyl chloride and succinoyl chloride. The reaction is conducted in a lower aliphatic ketone or nitrile in the presence of an acid-accepting amount of a pyridine derivative such as 2,6-lutidine. It has been found that the solvent properties of lower aliphatic ketones or nitriles and the basic properties of pyridine and its derivatives are particularly advantageous in a process for making bis(salicyl) diester cross-linking agents. Both the reactants and the pyridine of choice are quite soluble in lower aliphatic ketones and nitriles, but the pyridine derivative salt of the bis(salicyl) diester is insoluble in such solvents. Accordingly, as the bis(salicyl) diester is formed, it precipitates from the reaction medium as the pyridine salt. It has also been found that the major impurities and by-products remain soluble in the aliphatic ketone or nitrile solvent; therefore, a relatively high degree of purification is inherent in the process.

The salicylic acid compound and the lower aliphatic dicarboxylic acid halide are combined in approximately 2:1 stoichiometric amounts. If desired, a slight excess of the salicylic acid compound may be employed. For example, the mole ratio of salicylic acid compound to aliphatic dicarboxylic acid halide may range from about 5:1 to about 2:1, preferably from about 2.2:1 to 2:1. The concentration of the reactants in the lower aliphatic ketone or nitrile solvent may vary over a wide range. Such concentration preferably ranges from about 50 to about 200, preferably from about 80 to 90 grams of salicylic acid compound per liter of lower aliphatic ketone or nitrile solvent, with the concentration of the aliphatic dicarboxylic acid halide adjusted according to the above ratios.

To prevent hydrolysis of the aliphatic dicarboxylic acid halide or the bis(salicyl) diester product, the lower aliphatic ketone solvent advantageously is substantially anhydrous. Preferred solvents are acetone, methylethylketone, diethylketone, acetonitrile, proprionitrile, or butyronitrile, and the like. Acetone is particularly preferred.

The reaction solvent contains an acid-accepting amount of the pyridine derivative. Such amount will depend upon the concentration of the reactants in the solution. In general, a sufficient amount of the pyridine derivative is used to neutralize hydrogen ions generated as a result of the ester-forming reaction and to react with the bis(salicyl) diester product. A molar excess of the pyridine derivative is preferably used, e.g. from about 1 to 10, most preferably from about 1 to 3 moles of 2,6-lutidine or other pyridine derivative per mole of bis(salicyl) diester product generated.

The reactants may be added to the reaction medium in any order. A preferred means of carrying out the reaction is to dissolve the salicylic acid compound and the aliphatic dicarboxylic acid halide in the lower aliphatic ketone or nitrile solvent and then to add the pyridine derivative under substantially anhydrous conditions. The reaction of the acid halide with the salicylic acid compound is rapid and exothermic. The temperature of the reaction advantageously ranges from about 0° to about 40° C., preferably about 35°.

Upon completion of the ester-forming reaction, the insoluble bis(salicyl) diester 2,6-lutidine or pyridine salt is separated from the reaction mixture, e.g. by filtration or centrifugation. The solids may be washed with cold lower aliphatic ketone or nitrile solvent to remove further impurities. The desired bis(salicyl) diester product may be recovered from its 2,6-lutidine or other pyridine derivative salt by acidification and recrystallization. Such recovery procedure is initiated by dispersing the salt in a recrystallization solvent which may be any organic solvent in which the salt is substantially insoluble, and the bis(salicyl) diester is soluble. Preferred solvents for this purpose include dioxane, tetrahydrofuran, dimethoxyethane, and the lower aliphatic ketones or nitriles used as the reaction solvent. Preferably, the recrystallization solvent is water-miscible.

A preferred recrystallization procedure involves slowly adding an aqueous mineral acid (e.g. hydrochloric acid) to the dispersion of the salt to dissolve it. Addition of the aqueous mineral acid is continued until the bis(salicyl) diester product precipitates. The precipitate is then recovered, washed, and dried to yield the final product. Although a preferred means for recovering the bis(salicyl) diester from its pyridine derivative salt has been described, other recovery procedures will occur to those experienced in the art.

The overall yields of purified product resulting from the process of the present invention range from about 50 to 70 percent, compared to yields of 25 to 30 percent after recrystallization of crude products obtained from processes described in the prior art. The invention is further illustrated by the following Examples.

EXAMPLE 1

34 ml (0.315 mol) of fumaroyl chloride was added slowly over the course of 1.5 hours to a stirred solution of 3,5-dibromosalicylic acid (186.4 g, 0.63 mol) and 2,6-lutidine (147 ml, 1.26 mol) in 1.1 liter acetone (pre-dried over magnesium sulfate). The reaction mixture was stirred at room temperature for 2.5 hours after the addition of fumaroyl chloride was completed. A relatively crude 2,6-lutidine salt of the desired bis(3,5-dibromosalicyl) fumarate precipitated and was separated by filtration and then washed. The washing procedure was conducted in three phases; the salt was first washed with acetone until the washing is colorless, then with 1.7 liters of cold 0.29 M hydrochloric acid, and finally with 1 liter of cold water.

The crude, wet product was suspended in 1.7 liters of dioxane and the mixture was stirred for 10 minutes. A cold solution of 1 M HCl (500 ml) in water (1.2 liters) was added slowly until all solids were dissolved (about 500 ml of acid solution was required). Further slow addition of acid solution precipitated the desired free bis(3,5-dibromosalicyl) fumarate product. Additional water (850 ml) was added and the slurry was stirred at room temperature for 1 hour. Bis(3,5-dibromosalicyl) fumarate was isolated by filtration and washed with dioxane-water (1:1 v/v, 400 ml).

Further purification by recrystallization with dioxane-water was completed as follows. The bis(3,5-dibromosalicyl) fumarate isolated above was suspended in 650 ml dioxane and the mixture was gently heated to dissolve all solids. The solution was cooled to room temperature, and 240 ml water was added slowly with stirring to precipitate the product. After stirring for 30 minutes, the purified bis(3,5-dibromosalicyl) fumarate (134 g) was isolated by filtration. Addition of water (400 ml) to the filtrate gave a further 24.7 g of bis(3,5-dibromosalicyl) fumarate. Thus, a total yield of pure bis(3,5-dibromosalicyl) fumarate of 153 g (0.214 mol, 67.9 percent of theoretical) was obtained. $^1$H-NMR analysis of the product in dimethyl sulfoxide-d$_5$ indicates that the final product contains approximately 0.5 equivalents dioxane.

EXAMPLE 2

A solution of fumaroyl chloride (34 ml, 0.315 mol) was added rapidly and in one portion to a stirred solution of 3,5-dibromosalicylic acid (186.4 g, 0.63 mol) in dry acetone (1000 ml). Stirring was continued while a solution of 2,6-lutidine (147 ml, 1.26 mol) in dry acetone (100 ml) was added over 1.5 hours. After stirring at room temperature for an additional 3 hours, the crude intermediate product (the lutidine salt) was separated by filtration and washed, first with acetone until the filtrate became colorless, then with cold 0.3 M hydrochloric acid (2 liters), and finally with cold water (1 liter).

The crude material was suspended in acetone (2 liters), and the mixture was stirred for 15 minutes. A cold solution of 1 M hydrochloric acid (500 ml) in water (2 liters) was slowly added. Additional water (250 ml) was added, and the slurry was stirred at room temperature for 1 hour. Bis(3,5-dibromosalicyl) fumarate was isolated by drying in vacuo, yielding 120 g (57 percent of theoretical) of pure product. $^1$H-NMR analysis of the product in dimethyl sulfoxide-d$_6$ indicated that the final product contains less than 0.5 percent by weight of residual acetone.

That which is claimed is:

1. A process for the preparation of bis(salicyl) diesters, comprising:
   (a) reacting an aromatic hydroxy acid of the formula:

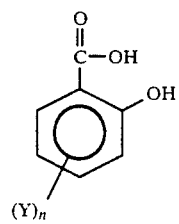

with a lower aliphatic dicarboxylic acid halide of the formula:

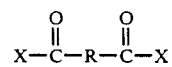

in a lower aliphatic ketone or nitrile solvent which contains an acid-accepting amount of 2,6-lutidine to produce an insoluble salt;
   (b) separating the insoluble salt from the reaction mixture of step (a), wherein R is a lower alkyl or alkylene of from 1 to about 5 carbon atoms; Y is hydrogen, chloro, bromo, iodo, fluoro, nitro, cyano, or trifluoromethyl; n is 1 or 2; and X is chloride or bromide.

2. The process of claim 1 together with the further step of recovering the desired bis(salicyl) diester from the insoluble salt.

3. A process of claim 2 wherein said recovering step comprises recrystallization with a mixture of a recrystallization solvent and a mineral acid.

4. A process of claim 3 wherein said recrystallization solvent is tetrahydrofuran.

5. A process of claim 3 wherein said recrystallization solvent is a lower aliphatic ketone or nitrile.

6. A process of claims 1 or 2 wherein said aliphatic dicarboxylic acid halide is fumaroyl chloride or succinyl chloride.

7. A process of claims 1 or 2 wherein said aromatic hydroxy acid is 3,5-dibromosalicylic acid.

8. A process for preparing bis(3,5-dibromosalicyl) fumarate, comprising:
   (a) adding 2,6-lutidine to a solution of 3,5-dibromosalicylic acid and fumaroyl chloride in a lower aliphatic ketone or nitrile solvent;
   (b) separating the resulting insoluble lutidine salt of bis(3,5-dibromosalicyl) fumarate,
   (c) suspending said salt in acetone or acetonitrile;
   (d) acidifying the suspension of salt; and
   (e) recovering free bis(3,5-dibromosalicyl) fumarate.

* * * * *

UNITED STATES PATENT AND TRADEMARK OFFICE
CERTIFICATE OF CORRECTION

PATENT NO.   :  5,041,615

DATED        :  August 20, 1991

INVENTOR(S)  :  Ton That Hai, Deanna J. Nelson, Ana Srnak

It is certified that error appears in the above-identified patent and that said Letters Patent is hereby corrected as shown below:

Column 1, between the title and the heading "Background of the Invention", insert the following paragraph:

--This invention was made with government support under Contract DAMD17-85-C-5194 awarded by the Department of the Army--

Signed and Sealed this

Twenty-seventh Day of October, 1992

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO.  : 5,041,615

DATED       : Aug. 20, 1991

INVENTOR(S) : Ton That Hai, Deanna J. Nelson, Ana Srnak

It is certified that error appears in the above-identified patent and that said Letters Patent is hereby corrected as shown below:

Column 1, line 8, before the BACKGROUND OF THE INVENTION, insert the following:

--This invention was made with government support under Contract DAMD17-85-C-5194 awarded by the Department of the Army. The Government has certain rights in this invention.--.

Signed and Sealed this

Fifth Day of January, 1993

Attest:

DOUGLAS B. COMER

Attesting Officer

Acting Commissioner of Patents and Trademarks